US012478303B2

(12) United States Patent
Zhang

(10) Patent No.: US 12,478,303 B2
(45) Date of Patent: Nov. 25, 2025

(54) LANCET DEVICE

(71) Applicant: TIANJIN HUAHONG TECHNOLOGY CO., LTD., Tianjin (CN)

(72) Inventor: Libo Zhang, Tianjin (CN)

(73) Assignee: TIANJIN HUAHONG TECHNOLOGY CO., LTD., Tianjin (CN)

( * ) Notice: Subject to any disclaimer, the term of this patent is extended or adjusted under 35 U.S.C. 154(b) by 973 days.

(21) Appl. No.: 16/872,547

(22) Filed: May 12, 2020

(65) Prior Publication Data

US 2020/0352495 A1 Nov. 12, 2020

(30) Foreign Application Priority Data

May 12, 2019 (CN) ......................... 201910391368.8

(51) Int. Cl.
*A61B 5/151* (2006.01)
*A61B 5/15* (2006.01)

(52) U.S. Cl.
CPC .... *A61B 5/15117* (2013.01); *A61B 5/150198* (2013.01); *A61B 5/150412* (2013.01);
(Continued)

(58) Field of Classification Search
CPC .......... A61B 5/150412; A61B 5/15117; A61B 5/15113; A61B 5/1519; A61B 5/15194
See application file for complete search history.

(56) References Cited

U.S. PATENT DOCUMENTS 5,730,753 A 3/1998 Morita
5,971,941 A * 10/1999 Simons ............. A61B 5/14532 600/583

(Continued)

FOREIGN PATENT DOCUMENTS

CN 203042258 U 7/2013
CN 203328703 U 12/2013
WO 2015115765 A1 8/2015

OTHER PUBLICATIONS

Office Action for corresponding Chinese Application No. 201910391368.8, dated Jul. 18, 2022.

(Continued)

*Primary Examiner* — Jennifer Robertson
*Assistant Examiner* — H. Q. Nguyen
(74) *Attorney, Agent, or Firm* — Scully, Scott, Murphy & Presser, P.C.

(57) ABSTRACT

Disclosed is a lancet device including: a body, having a first end and a second end; a head cap, wherein the first end of the head cap is provided with a needle outlet hole, and the second end of the head cap is connected to the first end of the body; a tail cap, wherein the first end of the tail cap is connected to the second end of the body, and the tail cap is provided with a first spring connecting portion, or the first spring connecting portion is provided in the tail cap; a needle core assembly, at least a part of which is axially guided and located in the body, wherein the needle core assembly includes a needle seat and a blood taking needle, the blood taking needle is provided on the needle seat, and the needle tip of the blood taking needle is adapted to extend out from the needle outlet hole; a trigger assembly, having a driving core acting on the needle seat, wherein the driving core is adapted to drive the needle seat to move toward the needle outlet hole based on a trigger operation, and the driving core is provided with a second spring connecting portion; a (Continued)

driving spring, the both ends of which respectively abut against or are connected with first and second spring connecting portions, wherein the driving spring is located between the first and second spring connecting portions; and an elastic force adjustment unit for adjusting the axial distance between the first and second spring connecting portions to adjust the trigger elastic force of the driving spring.

13 Claims, 8 Drawing Sheets

(52) U.S. Cl.
CPC .... *A61B 5/150633* (2013.01); *A61B 5/15113* (2013.01); *A61B 5/1519* (2013.01); *A61B 5/15194* (2013.01)

(56) References Cited

U.S. PATENT DOCUMENTS

| | | | | |
|---|---|---|---|---|
| 8,211,036 | B2 * | 7/2012 | Schraga | A61B 5/15186 600/583 |
| 2003/0100913 | A1 | 5/2003 | Shi | |
| 2003/0187470 | A1 | 10/2003 | Chelak et al. | |
| 2006/0259059 | A1 * | 11/2006 | Marshall | A61B 5/15117 606/181 |
| 2009/0030442 | A1 * | 1/2009 | Potter | A61B 5/150916 606/182 |
| 2020/0253523 | A1 * | 8/2020 | Shi | A61B 5/150198 |

OTHER PUBLICATIONS

Decision on Rejection and English translation for corresponding Chinese Application No. 201910391368.8, dated Jan. 19, 2023.

* cited by examiner

LANCET DEVICE

CROSS-REFERENCE TO RELATED PATENT APPLICATIONS

This application claims the benefit of priority of Chinese Patent Application number 201910391368.8 filed May 12, 2019, which is incorporated by reference herein in its entirety.

FIELD OF THE INVENTION

Embodiments of the present disclosure relate to the field of medical devices, and in particular, to a lancet device.

BACKGROUND OF THE INVENTION

A known lancet device includes a lancet device body and a head cap, and a blood taking needle is installed in the lancet device body. The head cap includes: a head cap housing; a connecting cylinder, wherein the head cap housing is rotatably connected to the connecting cylinder relative to the connecting cylinder; a head cap core installed in a space formed by the head cap housing and the connecting cylinder, wherein based on the rotation of the head cap housing, the head cap core moves along the longitudinal center line while rotating, and the head cap core is provided with a blocking surface that defines the puncture depth of the blood taking needle.

The relative puncture depth of the blood taking needle of the lancet device is generally adjusted in the following manner: after the axial movement of a head cap driving core in the space formed by the head cap housing and the connecting cylinder, the gap between the blocking surface of the head cap driving core and the head cap housing is increased or decreased to control the puncture depth of the blood taking needle.

Although the puncture depth of the blood taking needle of the known lancet device can be adjusted, for people with different skin types, the same elastic force still cannot simultaneously meet the needs of low pain and sufficient blood volume. In addition, the blood taking needle is prone to jitter during the puncture process, which increases the pain of a user. In addition, the structure of adjusting the puncture depth of the blood taking needle of the known lancet device is relatively complicated.

SUMMARY OF THE INVENTION

In order to alleviate or solve at least one aspect of the above problems, the present disclosure is proposed.

According to one aspect of the embodiments of the present disclosure, the present disclosure provides a lancet device, including:

- a body;
- a needle seat and a blood taking needle, wherein the needle seat is provided in the body, the blood taking needle is provided on the needle seat, and the needle tip of the blood taking needle is adapted to extend out from a needle outlet hole of the lancet device;
- a driving core, which is adapted to drive the needle seat to move toward the needle outlet hole;
- a driving spring for providing a trigger elastic force for the driving core; and
- an elastic force adjustment unit for adjusting the axial distance between the two ends of the driving spring to adjust the magnitude of the trigger elastic force.

According to another aspect of the embodiments of the present disclosure, a lancet device is further proposed, including:

- a body, having a first end and a second end;
- a head cap, wherein the first end of the head cap is provided with a needle outlet hole, and the second end of the head cap is connected to the first end of the body;
- a tail cap, wherein the first end of the tail cap is connected to the second end of the body, and the tail cap is provided with a first spring connecting portion, or a first spring connecting portion is provided in the tail cap;
- a needle core assembly, at least a part of which is axially guided and located in the body, wherein the needle core assembly includes a needle seat and a blood taking needle, the blood taking needle is provided to the needle seat, and the needle tip of the blood taking needle is adapted to extend out from the needle outlet hole;
- a trigger assembly, having a driving core acting on the needle seat, wherein the driving core is adapted to drive the needle seat to move toward the needle outlet hole based on a trigger operation, and the driving core is provided with a second spring connecting portion;
- a driving spring for providing power for the needle seat to move toward the needle outlet hole, wherein the first end of the driving spring is adapted to abut against or connecting with the second spring connecting portion, the second end of the driving spring is adapted to abut against or connecting with the first spring connecting portion, and the driving spring is located between the first spring connecting portion and the second spring connecting portion; and
- an elastic force adjustment unit for adjusting the axial distance between the first spring connecting portion and the second spring connecting portion to adjust the trigger elastic force of the driving spring.

BRIEF DESCRIPTION OF THE DRAWINGS

FIG. 2-1 to FIG. 2-4 are schematic diagrams of a needle seat of a lancet device according to an exemplary embodiment of the present disclosure;

FIG. 3-1 to FIG. 3-2 are schematic diagrams of a stop block of a lancet device according to an exemplary embodiment of the present disclosure;

FIG. 4-1 to FIG. 4-4 are schematic diagrams of a guide sleeve of a lancet device according to an exemplary embodiment of the present disclosure;

FIG. 6-1 to FIG. 6-4 are schematic diagrams of a cylinder of a lancet device according to an exemplary embodiment of the present disclosure;

FIG. 7-1 to FIG. 7-2 are schematic diagrams of a button of a lancet device according to an exemplary embodiment of the present disclosure;

FIG. 8-1 to FIG. 8-4 are schematic diagrams of a tail cap core of a lancet device according to an exemplary embodiment of the present disclosure;

FIG. 10-1 to FIG. 10-3 are schematic diagrams of a tail cap housing of a lancet device according to an exemplary embodiment of the present disclosure;

FIG. 12-1 to FIG. 12-3 are schematic diagrams of a second blocking piece of a lancet device according to an exemplary embodiment of the present disclosure;

FIG. 14-1 to FIG. 14-2 are sectional views of a lancet device in maximum and minimum states of puncture distance and elastic force according to an exemplary embodiment of the present disclosure when a driving spring is in a free state;

FIG. 15-1 to FIG. 15-2 are sectional views of a lancet device in maximum and minimum states of puncture distance and elastic force according to an exemplary embodiment of the present disclosure when a driving spring is in a pre-pressed state;

FIG. 16-1 to FIG. 16-2 are sectional views of a needle tip puncture distance in maximum and minimum states of puncture distance and elastic force of a lancet device according to an exemplary embodiment of the present disclosure;

DETAILED DESCRIPTION OF THE EMBODIMENTS

Figures 1, 2:
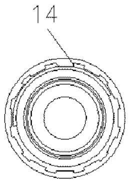
FIG. 1-1 to FIG. 1-4 are schematic diagrams of a cap of a lancet device according to an exemplary embodiment of the present disclosure.
Figure 1:
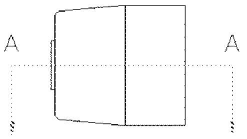
Figures 1, 2, 3:
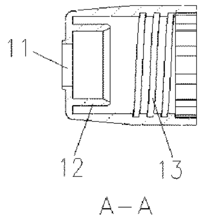

The technical solutions of the present disclosure are further described in detail below through the embodiments and the drawings. In the description, the same or similar reference signs indicate the same or similar components. The following description of the embodiments of the present disclosure with reference to the drawings is intended to explain the general inventive concept of the present disclosure, and should not be construed as a limitation of the present disclosure.

The structure and installation of a lancet device according to an exemplary embodiment of the present disclosure are described below with reference to the drawings. It should be pointed out that, for the clarity of display, some features or components in some drawings are not specifically shown.

A needle seat 20 is provided with a needle seat groove 21 in the direction of a needle outlet hole to accommodate and fix a blood taking needle 50 (referring to FIG. 14-1 and FIG. 14-2); and the needle seat groove 21 is provided with a plurality of elastic pieces 23 on the periphery (referring to FIG. 2-4), and the maximum outer diameter of an outer side wall of the elastic piece 23 is slightly greater than the inner diameter of a limiting rib 12 (referring to FIG. 1-3 and FIG. 14-1 and FIG. 14-2). During a blood collection process, the needle seat 20 moves back and forth in a cap 10 axially, and the needle seat 20 moves smoothly via the deformation of the elastic pieces 23, thereby reducing the jitter of the blood taking needle during the blood collection process and reducing the pain of the user.

A guide rib 27 is installed in a guide sleeve 40 along a first guide groove 48 (referring to FIG. 4-2), until a second matching surface 28 is in contact with a front end face 41.

A column 33 of a stop block 30 is installed via a through hole 25 in a state that a first catching piece 34 is caught by a first matching surface 26, and a second catching piece 35 is caught by a notch 24.

The guide sleeve 40 in which the needle seat 20 and the stop block 30 are installed is installed in a housing 60, a button 70 has been placed in the housing 60 in advance, a trigger surface 72 is exposed to the outside of the housing 60 through a button hole 63, an edge 71 is retained in the housing 60, and a contact point 73 is close to a needle outlet hole 11; a first hook 43 is retained on the same side as the button hole 63, and an assembling groove 44 is installed along a mounting rib 61, until a first positioning surface 45 abuts against a front end face 66.

A cap 10 is an internally hollow housing and is provided to the guide sleeve 40 in a sleeving manner, a first thread groove 13 is screwed onto a first thread rib 42, the cap 10 can move along the axial direction in a departing manner or an approaching manner through the cooperation of the first thread groove 13 and the first thread rib 42; when a bottom surface 15 abuts against a second positioning surface 49 (referring to FIG. 4-1), the cap 10 is located at the nearest end, at this time, the puncture depth of the blood taking needle is the maximum, and when the first hook 43 at the farthest end acts on a blocking surface 14, the puncture depth of the blood taking needle is the minimum. One end of the cap 10 is provided with the needle outlet hole 11, so that the blood taking needle can be installed in the body and can perform the puncturing; a circle of limiting rib 12 (forming an annular wall, and the annular wall can also be an intermittent structure in the circumferential direction) is provided around the needle outlet hole 11, and the space formed between the limiting rib 12 and the housing of the cap 10 can accommodate a part of a spring 140 so as to limit the amount of circumferential swing of the spring 140 (referring to FIG. 14-1 and FIG. 14-2).

Figures 1, 2, 3, 4:
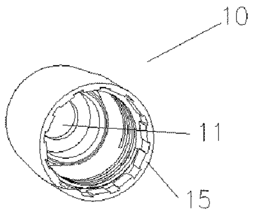
Figures 1, 2:
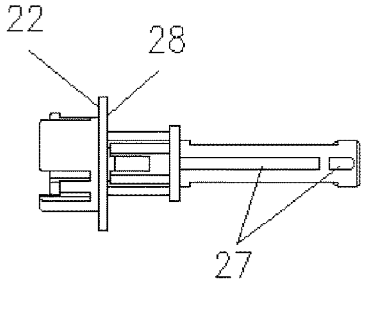
Figures 2, 3:
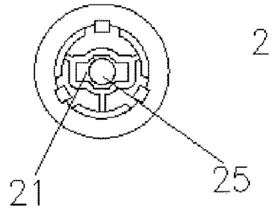
Figures 2, 3, 4:
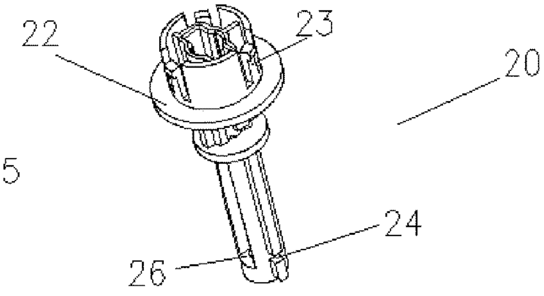
Figure 2:
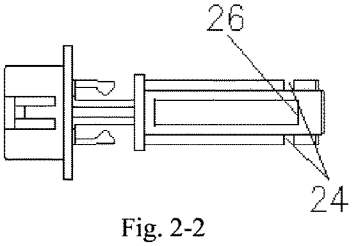
Figures 1, 3:
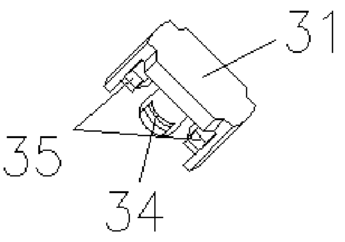
Figures 2, 3:
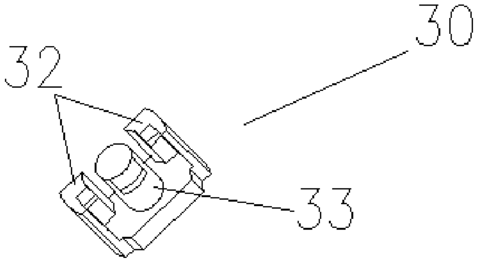
Figures 2, 4:
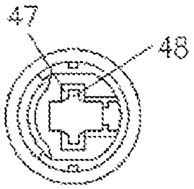
Figures 1, 4:
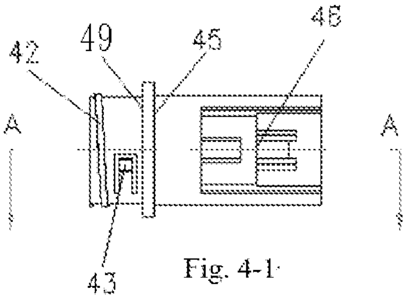
Figure 4:
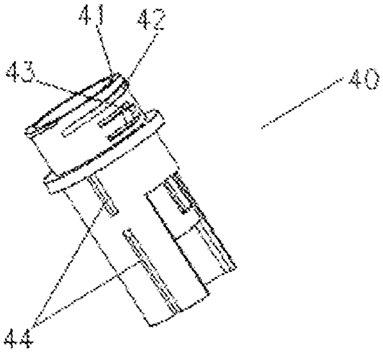
Figures 3, 4:
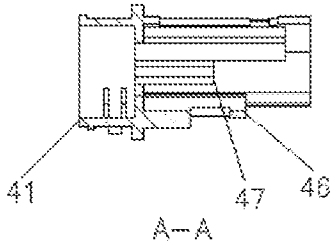
Figure 5:
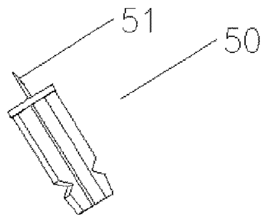
FIG. 5 is a schematic diagram of a blood taking needle of a lancet device according to an exemplary embodiment of the present disclosure.
Figures 2, 6:
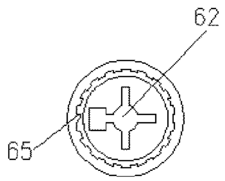
Figures 1, 6:
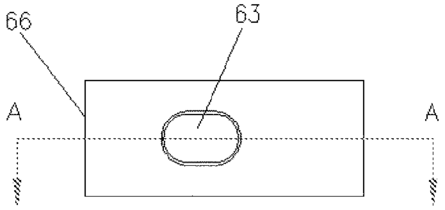
Figures 4, 6:
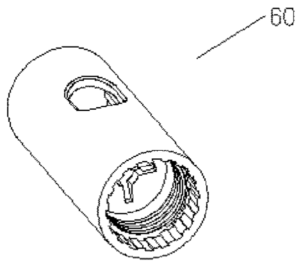
Figures 3, 6:
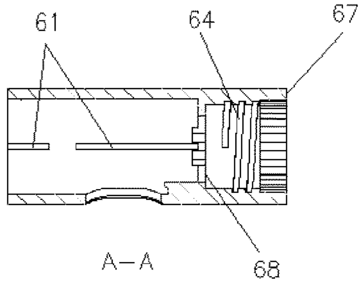
Figures 1, 7:
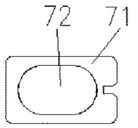
Figures 2, 7:
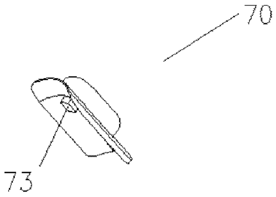
Figures 1, 8:
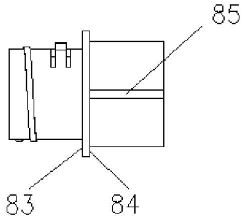
Figures 2, 8:
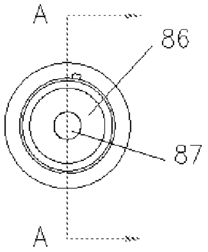
Figures 3, 8:
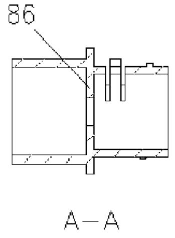
Figures 4, 8:
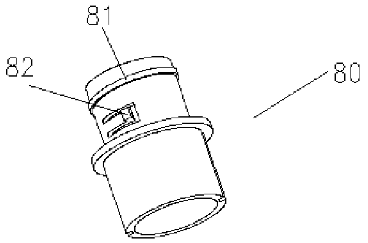
Figure 9:
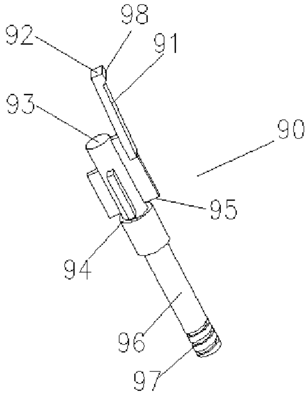
FIG. 9 is a schematic diagram of a driving core of a lancet device according to an exemplary embodiment of the present disclosure.
Figures 1, 10:
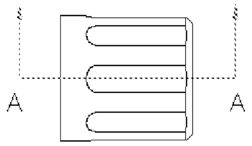
Figures 2, 10:
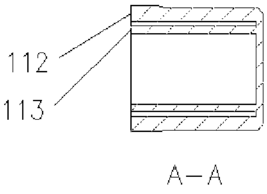
Figures 3, 10:
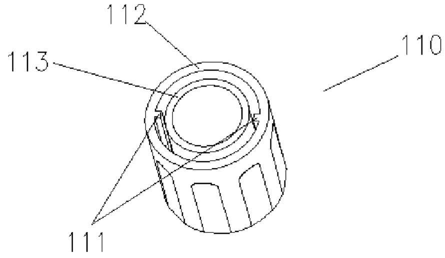
Figure 11:
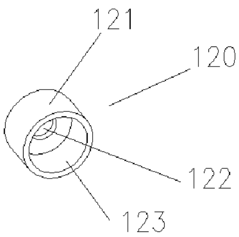
FIG. 11 is a schematic diagram of a first blocking piece of a lancet device according to an exemplary embodiment of the present disclosure.
Figures 1, 12:
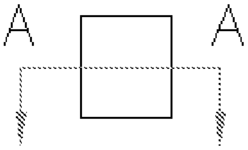
Figures 2, 12:
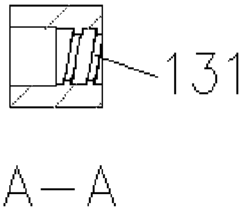
Figures 3, 12:
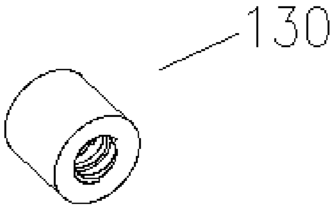
Figure 13:
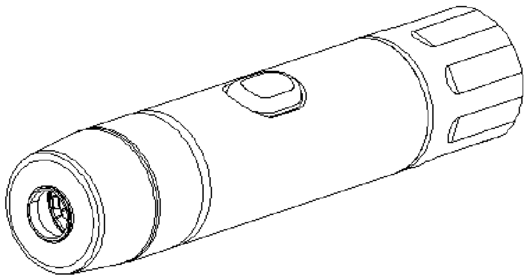
FIG. 13 is a three-dimensional schematic diagram of a lancet device according to an exemplary embodiment of the present disclosure.
Figures 1, 14:
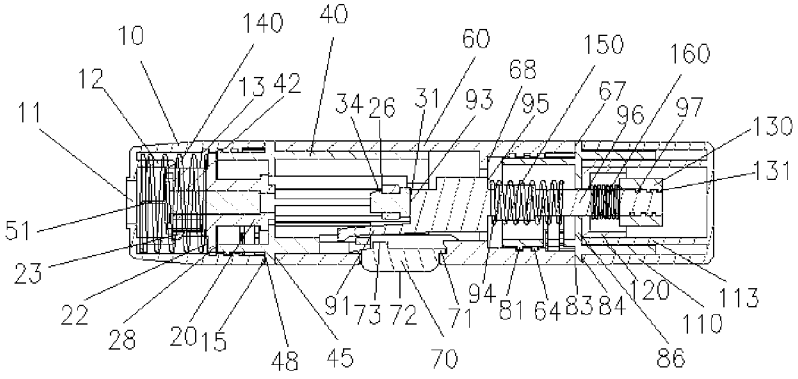
Figures 2, 14:
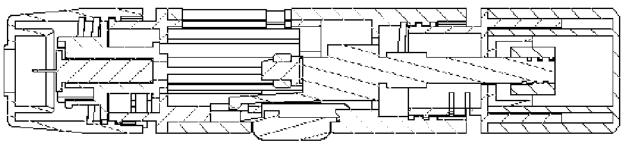

A spring 150 is provided to a column 96 of a driving core 90 in a sleeving manner (referring to FIG. 14-1 and FIG. 14-2), and then the column 96 is installed into a tail cap core 80 in a direction of facing a second thread rib 81, the tail cap core 80 is divided into two parts by a separation piece 86, a first through hole 87 is formed in the middle of the separation piece for the passage of the column 96; then, a first blocking piece 120 is provided to the column in the sleeving manner, and an opening 123 of the first blocking 120 faces toward a second thread groove 97 of the driving core 90; the first blocking piece 120 is a cylindrical housing provided with a second through hole 122 at one end, the outer diameter of the first blocking piece 120 is greater than that of the first through hole 87, so that the first blocking piece 120 is blocked by the separation piece 86, and then a spring 160 is provided to the column 96 in the sleeving manner (referring to FIG. 14-1 and FIG. 14-2); and a second blocking piece 130 is a cylinder provided with a through hole therein, a part of the through hole is provided with a third thread 131, the part without the thread of the second blocking piece 130 faces toward the spring 160, the third thread 131 is screwed to the second thread groove 97, and the spring 160 can be arranged between the first blocking piece 120 and the second blocking piece 130 (referring to FIG. 14-1 and FIG. 14-2).

A tail cap 110 is a housing provided with an opening at one end, the tail cap includes therein a circle of rib 113, the inner diameter of the rib 113 is less than the outer diameter of the first blocking piece 120, so that the first blocking piece 120 is in interference fit with the rib 113, the foregoing inner core assembly is installed from the opening of the tail cap 110, and a second guide groove 85 is aligned with a positioning rib 111, until an end face 112 is in contact with a fourth positioning surface 84. The driving core 90 of this assembly passes through a second through hole 62 (referring to FIG. 19, FIG. 6-1 to FIG. 6-4, and FIG. 9), an elastic arm 91 is aligned with a button hole 63, and the second thread rib 81 is in screw connection with a second thread groove 64 of the foregoing main body assembly, until a third positioning surface 83 abuts against a rear end face 67 (referring to FIG. 14-1 and FIG. 14-2). The entire lancet device is assembled.

The operation of the lancet device according to the exemplary embodiment of the present disclosure will be described below with reference to the drawings. It should be pointed out that, for the clarity of display, some features or components in some drawings are not specifically shown.

Figures 1, 15:
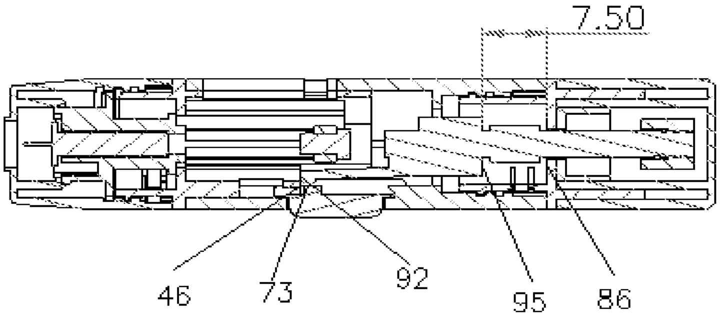
Figures 2, 15:
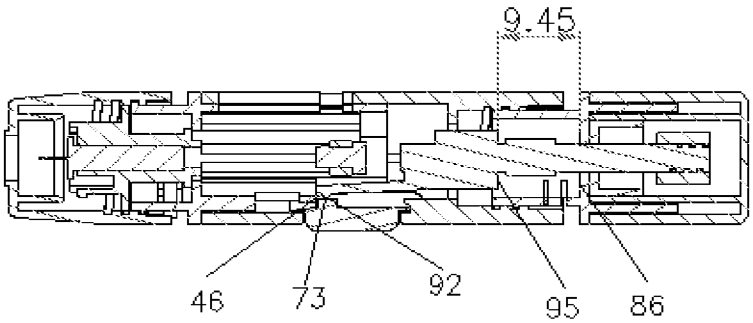
Figure 17:
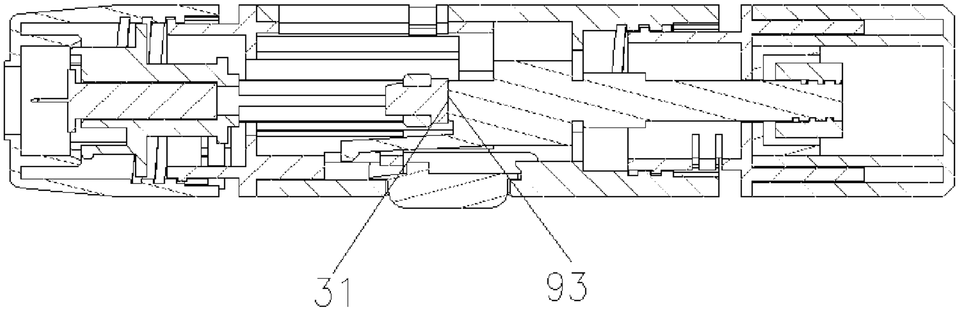
FIG. 17 exemplarily shows a schematic diagram of a trigger process, wherein the puncture distance and the elastic force are in the minimum state.
Figure 18:
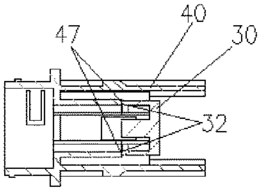
FIG. 18 exemplarily shows the cooperation of the guide sleeve and the stop block during the puncture of the needle tip.
Figure 19:
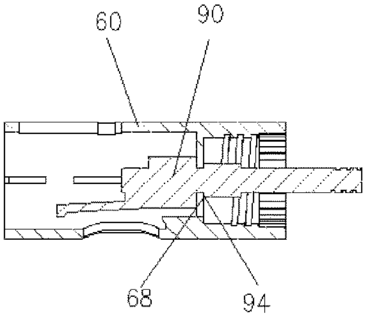
FIG. 19 exemplarily shows the cooperation of the driving core and the body during a trigger process.

During blood collection, the blood taking needle 50 is installed and fixed in the needle seat groove 21 through the needle outlet hole 11, the tail cap is pulled to drive the driving core 90 to axially move to depart from the needle outlet hole 11, until the elastic arm 91 slides over a second positioning surface 46, a first top face 92 abuts against the second positioning surface 46, the spring 150 is compressed by a fifth positioning surface 95, and the lancet device enters a state to be triggered (referring to FIG. 15-1); and the button 70 is pressed, the contact point 73 is in contact with a protrusion 98 to deform the elastic arm 91, the first top face 92 deviates from the control of the second positioning surface 46, so that the limitation to the driving core 90 is removed, the elastic force released from the compressed state of the spring 150 drives the driving core 90 to move instantly toward the direction of the needle outlet hole 11, until a third stop surface 94 hits a matching surface 68. Before the driving core 90 stops moving, a second top face 93 has hit a transmission surface 31 (referring to FIG. 17), the impact force drives the needle seat 20 to move, a needle tip portion 51 of the blood taking needle is exposed from a needle outlet, when a first stop surface 32 hits a second stop surface 47 (referring to FIG. 18), the needle seat 20 stops moving toward the direction of the needle outlet hole, and under the promotion of the spring 140, the needle tip of the blood taking needle retracts into the lancet device to complete the blood collection. The stop block 30 can be made of a soft rubber material to reduce the vibration during the impact.

Figures 1, 16:
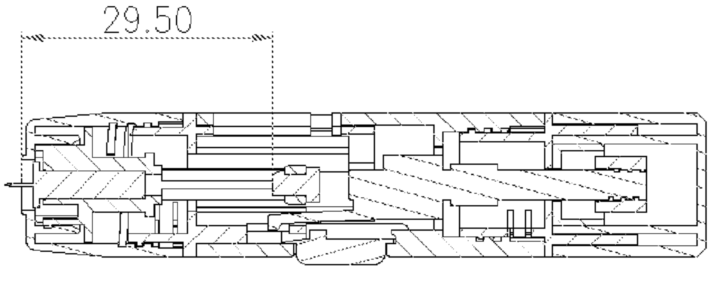
Figures 2, 16:
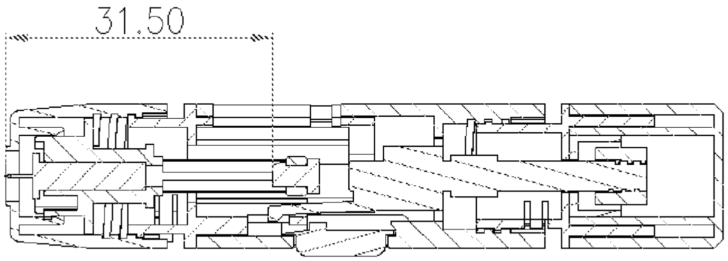
Figure 20:
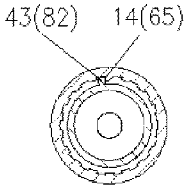
FIG. 20 exemplarily shows the cooperation of a hook and a blocking surface.

Preparatory works that can be made before blood collection include: 1. the puncture length of the blood taking needle is adjusted: the cap is rotated, because during a trigger process, the needle seat 20 will stop moving toward the direction of the needle outlet hole at the arrival of a specified position, the puncture length of the needle tip of the blood taking needle can be adjusted by the axial movement of the cap (referring to FIG. 16-1 and FIG. 16-2). 2. The elastic force when the spring 150 is triggered is adjusted: when the tail cap 110 is rotated, since the compression of the spring 150 is limited by the fifth positioning surface 95 and the separation piece 86 (referring to FIG. 15-1 and FIG. 15-2), the second thread rib 81 of the tail cap core 80 is driven by the positioning rib 111 to rotate along the second thread groove 64, in this case, when the fourth positioning surface 84 is in close contact with the rear end face 67, the tail cap core 80 is located at the nearest end, the compression amount of the spring is the maximum, and the elastic force is the maximum (referring to FIG. 15-1); and when the tail cap core 80 is rotated until a second hook 82 is in contact with a second blocking surface 65 (referring to FIG. 20), the tail cap core 80 cannot move further toward the far end due to the limitation of the second blocking surface 65, at this time, the tail cap core is located at the furthest end, the distance between the fifth positioning surface 95 and the separation piece 86 is the maximum, the compression amount of the spring is the minimum, and the elastic force is the minimum (referring to FIG. 15-2). The user can adjust the punctuate length and strength between the minimum and the maximum to suit his own needs.

In the above embodiment of the present disclosure, since the compression of the spring 150 is limited by the fifth positioning surface 95 and the separation piece 86, when the tail cap 110 is rotated, the second thread rib 81 of the tail cap core 80 is driven by the positioning rib 111 to rotate along the second thread groove 64, when the fourth positioning surface 84 is in close contact with the rear end face 67, the tail cap core 80 is located at the nearest end, the compression amount of the spring is the maximum, and the elastic force is the maximum; and when the tail cap core 80 is rotated until the second hook 82 is in contact with the second blocking surface 65, the tail cap core 80 cannot move further toward the far end due to the limitation of the second blocking surface 65, at this time, the tail cap core is located at the furthest end, the distance between the fifth positioning surface 95 and the separation piece 86 is the maximum, the compression amount of the spring is the minimum, and the elastic force is the minimum.

By adjusting the magnitude of the elastic force of the spring 150 (i.e, the driving spring), the needle ejection speed can be adjusted. Generally speaking, the faster the needle ejection speed is, the lower the pain of the user is in the case of not considering other factors.

In the embodiment of the present disclosure, a plurality of elastic pieces 23 are provided to the periphery of the needle seat groove 21, the needle seat 20 axially reciprocates in the cap 10 during the blood collection process, and the needle seat 20 moves smoothly via the deformation of the elastic pieces 23 (acting with the limiting rib 12), thereby reducing the jitter of the blood taking needle during the blood collection process and reducing the pain of the user.

In the embodiment of the present disclosure, the space formed by the limiting rib 12 and the housing of the cap 10 can accommodate a part of the spring 140 so as to limit the amount of circumferential swing of the spring 140, so that the jitter of the blood taking needle during the blood collection process can be reduced, and the pain of the user can be alleviated.

In the embodiment of the present disclosure, by using the stop block made of a soft material, the vibration during the impact of the driving core and the needle seat can be reduced, and the pain of the user can be alleviated.

In the embodiment of the present disclosure, the adjustment of the puncture depth is realized just by adjusting the relative axial position between the head cap and the body, which, compared with the known technique of driving the head cap core to rotate via the rotation of the head cap, the number of components for adjusting the puncture depth is reduced.

In the embodiment of the present disclosure, the adjustment of the puncture depth and the adjustment of the driving elastic force are both realized in the technical solution of the lancet device, which is conducive to further reducing the pain of the user. The embodiment of the present disclosure provides a lancet device, which takes the puncture depth and the puncture force (speed) of the blood taking needle at the same time.

In the embodiment of the present disclosure, although the needle seat and the driving core are two separate components, they can also be formed into one component, which is also within the protection scope of the present disclosure.

There can be many modifications to the above-described embodiment. For example:

the lancet device may be provided with the tail cap core and is not provided with the tail cap housing, or, the tail cap core and the tail cap housing are of an integrated structure;

the component connected to the second end of the driving spring (in the present disclosure, the end away from the needle outlet hole is the second end, and the end close to the needle outlet hole is the first end) can also be configured to move axially relative to the tail cap core, in addition to being fixedly connected to the tail cap core;

the driving spring can provide a driving force in a compressed state and can also provide the driving force in a stretched state;

when the driving spring provides the driving force in the compressed state, the adjustment of the magnitude of the elastic force may not be limited to adjusting the position of the second end of the driving spring, and the position of the first end of the driving spring can also be adjusted;

the axial distance between the two ends of the driving spring is adjusted or the axial distance between two connecting components is adjusted, a threaded connection can be adopted, and other manners can also be adopted, including snap fit connection or the like;

in the case that it is not necessary to use the head cap to adjust the puncture depth, the lancet device may not include the head cap, or, the head cap is directly integrated with the body of the lancet device;

in the case that it is not necessary to use the tail cap to locate the lancet device at a standby position to be triggered, the lancet device may not be provided with the tail cap, or the tail cap is directly integrated with the body of the lancet device; and the stop block may be not provided, but the puncture depth of the blood taking needle is selected or controlled through the cooperation between the driving spring and the return spring, so as to eliminate the pain caused by the lancet device to the user due to vibration.

The above modifications are all within the protection scope of the present disclosure Based on the above description, the present disclosure proposes the following solutions:

1. A lancet device, including:

a body;

a needle seat and a blood taking needle, wherein the needle seat is provided in the body, the blood taking needle is provided on the needle seat, and the needle tip of the blood taking needle is adapted to extend out from a needle outlet hole of the lancet device;

a driving core, which is adapted to drive the needle seat to move toward the needle outlet hole;

a driving spring for providing a trigger elastic force for the driving core; and an elastic force adjustment unit for adjusting the axial distance between the two ends of the driving spring to adjust the magnitude of the trigger elastic force.

2. The lancet device according to 1, further including:

a tail cap, wherein the first end of the tail cap is connected to the second end of the body, and the tail cap is provided with a first spring connecting portion, or a first spring connecting portion is provided in the tail cap, wherein:

the driving core is provided with a second spring connecting portion, the first end of the driving spring is adapted to abut against or connecting with the second spring connecting portion, the second end of the driving spring is adapted to abut against or connecting with the first spring connecting portion, and the driving spring is located between the first spring connecting portion and the second spring connecting portion; and the elastic force adjustment unit is provided to adjust the axial distance between the first spring connecting portion and the second spring connecting portion to adjust the trigger elastic force of the driving spring.

3. The lancet device according to 2, wherein:

the elastic force adjustment unit is adapted to adjust an axial position of the first spring connecting portion relative to the body.

4. The lancet device according to 3, wherein:

connection units capable of relatively moving in the axial direction are formed between the first end of the tail cap and the second end of the body, and the connection units form the elastic force adjustment unit.

5. The lancet device according to 4, wherein:

the connection units are threaded connection units between the first end of the tail cap and the second end of the body.

6. The lancet device according to 5, wherein:

the tail cap comprises a tail cap housing and a tail cap core, and the tail cap core is provided with a threaded connection portion that is in threaded connection with the second end of the body; and the tail cap core is provided in the tail cap housing in a manner of being able to axially move relative to the tail cap housing, and a cooperation structure for preventing the relative rotation of the tail cap core and the tail cap housing in the circumferential direction is provided therebetween.

7. The lancet device according to 6, wherein:

the tail cap is adapted to abut against the end face of the second end of the body, and the abutting position defines the position of the tail cap where the elastic force of the driving spring is the maximum.

8. The lancet device according to 7, wherein:

the tail cap core and the body are provided with snap fit structures for defining the position of the tail cap where the elastic force of the driving spring is the minimum.

9. The lancet device according to 5, wherein:

one of the tail cap and the body is provided with a thread, the other of the tail cap and the body is provided with a thread cooperation portion, the thread is in interference fit with the thread cooperation portion, or the thread and the thread cooperation portion are additionally provided with snap fit structures, and the snap fit structures are configured to limit the relative axial position between the tail cap and the body.

10. The lancet device according to 3, wherein:

the first spring connecting portion is applicable to moving relative to the main body of the tail cap along the axial direction; and the elastic force adjustment unit is configured to drive the first spring connecting portion to move relative to the main body of the tail cap in the axial direction.

11. The lancet device according to 2, wherein:
the elastic force adjustment unit is adapted to adjust the axial position of the second spring connecting portion relative to the body.

12. The lancet device according to 1, further including:
a head cap, wherein the first end of the head cap is provided with the needle outlet hole, and the second end of the head cap is connected to the first end of the body.

13. The lancet device according to 12, wherein:
the second end of the lancet device is provided with a first spring connecting portion that is adapted to abut against or connecting with the second end of the driving spring;
the driving core is provided with a second spring connecting portion, the first end of the driving spring is adapted to abut against or connecting with the second spring connecting portion; and
the elastic force adjustment unit is configured to adjust the axial relative distance between the body and the head cap, so as to adjust the axial distance between the first spring connecting portion and the second spring connecting portion to adjust the trigger elastic force of the driving spring.

14. The lancet device according to 13, further including:
a tail cap, wherein the first end of the tail cap is connected to the second end of the body, and the tail cap is provided with a first spring connecting portion, or a first spring connecting portion is provided in the tail cap.

15. The lancet device according to 1, further including:
a head cap, wherein the first end of the head cap is provided with the needle outlet hole, and the second end of the head cap is connected to the first end of the body;
wherein:
the head cap is provided with a first spring connecting portion that is applicable to connecting with the first end of the driving spring;
the driving core is provided with a second spring connecting portion, and the second end of the driving spring is connected to the second spring connecting portion; and
the elastic force adjustment unit is configured to adjust the axial relative distance between the body and the head cap, so as to adjust the axial distance between the first spring connecting portion and the second spring connecting portion to adjust the trigger elastic force of the driving spring 16. The lancet device according to 12, wherein:
the first end of the needle seat is provided with elastic arms that are evenly distributed in the circumferential direction, and the elastic arms elastically abut against an inner wall of the head cap or are provided on an annular wall in the head cap.

17. The lancet device according to 16, wherein:
the lancet device further includes a return spring, and the return spring is adapted to abut against between the head cap and the needle seat to provide an elastic force for retracting the ejected blood taking needle into the head cap.

18. The lancet device according to 17, wherein:
the elastic arms are provided to the annular wall in the head cap in an elastic abutting manner, and a space applicable to accommodating the return spring is defined between the annular wall and the inner wall of the head cap.

19. The lancet device according to 18, wherein:
the surface of the needle seat abutting against the return spring is a plane, and the abutting end portion of the return spring and the plane form surface contact.

20. The lancet device according to 1, further including:
a stop block provided at the second end of the needle seat, and the stop block cooperates with a corresponding blocking surface in the lancet device to define the movement position of the needle seat toward the needle outlet hole.

21. The lancet device according to 20, wherein:
the stop block comprises an elastomer.

22. The lancet device according to 12, wherein:
a connecting unit adapted to adjust the axial distance of the needle outlet hole of the head cap relative to the first end of the body is provided between the head cap and the body.

23. The lancet device according to 22, wherein:
the connecting unit includes a thread provided to one of the head cap and the body, and a thread cooperation portion provided to the other of the head cap and the body, the thread is in interference fit with the thread cooperation portion, or the thread and the thread cooperation portion are additionally provided with snap fit structures, and the snap fit structures are configured to limit the relative axial position between the head cap and the body.

24. The lancet device according to 23, wherein:
the body includes a cylinder and a guide sleeve, the first end of the cylinder is provided to the guide sleeve in a sleeving manner, and the guide sleeve is provided with the thread or the thread cooperation portion.

25. The lancet device according to 22, wherein:
a snap fit structure is additionally provided between the head cap and the body, and the snap fit structure is configured to limit the relative axial position between the head cap and the body.

26. A lancet device, including:
a body, having a first end and a second end;
a head cap, wherein the first end of the head cap is provided with a needle outlet hole, and the second end of the head cap is connected to the first end of the body;
a tail cap, wherein the first end of the tail cap is connected to the second end of the body, and the tail cap is provided with a first spring connecting portion, or the first spring connecting portion is provided in the tail cap;
a needle core assembly, at least a part of which is axially guided and located in the body, wherein the needle core assembly includes a needle seat and a blood taking needle, the blood taking needle is provided to the needle seat, and the needle tip of the blood taking needle is adapted to extend out from the needle outlet hole;
a trigger assembly, having a driving core acting on the needle seat, wherein the driving core is adapted to drive the needle seat to move toward the needle outlet hole based on a trigger operation, and the driving core is provided with a second spring connecting portion;
a driving spring for providing power for the needle seat to move toward the needle outlet hole, wherein the first end of the driving spring is adapted to abut against or connecting with the second spring connecting portion, the second end of the driving spring is adapted to abut against or connecting with the first spring connecting portion, and the driving spring is located between the first spring connecting portion and the second spring connecting portion; and an elastic force adjustment unit for adjusting the axial distance between the first spring connecting portion and the second spring connecting portion to adjust the trigger elastic force of the driving spring.

Although the embodiments of the present disclosure have been shown and described, it can be understood by those of ordinary skill in the art that, modifications can be made to these embodiments without departing from the principles and spirit of the present disclosure, and the scope of the present disclosure is defined by the appended claims and their equivalents.

What is claimed is:

1. A lancet device comprising:

a body having a first end and a rear second end;

a needle seat, wherein the needle seat is provided in the body, a blood taking needle is adapted to be provided on the needle seat, and a needle tip of the blood taking needle is configured to extend out from a needle outlet hole of the lancet device;

a driving core configured to drive the needle seat to move toward the needle outlet hole;

a driving spring for providing a trigger elastic force for the driving core;

a tail cap provided at a distalmost end of the lancet device opposite the blood taking needle, the tail cap comprising a tail cap housing and a tail cap core, the tail cap core being provided with a threaded connection portion that is in threaded connection with the rear second end of the body, the tail cap being provided with a first spring connecting portion, and the tail cap core being divided into two parts, a proximate end and a distal end, by a separation piece, wherein compression of the driving spring is limited by the separation piece, the separation piece comprising a proximate and distal end face, and the proximate end face of the separation piece is configured to abut against the rear second end face of the body, and the elastic force is the maximum at this position;

wherein the driving core is provided with a second spring connecting portion, a first end of the driving spring is configured to abut against or be connected with the second spring connecting portion of the driving core, a second end of the driving spring is configured to abut against or be connected with the first spring connecting portion of the tail cap, and the driving spring is located between the first spring connecting portion and the second spring connecting portion;

wherein the tail cap core is provided in the tail cap housing in a manner of being able to axially move relative to the tail cap housing without relative rotation; and wherein the tail cap is configured to be rotatable relative to the body to adjust an axial distance between the first spring connecting portion and the second spring connecting portion, to adjust the trigger elastic force of the driving spring.

2. The lancet device according to claim 1, wherein:

the tail cap is configured to rotate relative to the body to adjust an axial position of the first spring connecting portion relative to the body.

3. The lancet device according to claim 2, wherein:

threaded connection units capable of relatively moving in an axial direction are formed between a first end of the tail cap and the second end of the body.

4. The lancet device according to claim 2, wherein:

the first spring connecting portion is applicable to moving relative to the tail cap housing along an axial direction; and the tail cap is configured to rotate relative to the body to drive the first spring connecting portion to move relative to the tail cap housing in the axial direction.

5. The lancet device according to claim 1, wherein:

the tail cap core is formed with a guide groove, and the guide groove is aligned with and engages a positioning rib provided to the tail cap housing to prevent a relative rotation of the tail cap core and the tail cap housing in a circumferential direction is provided therebetween.

6. The lancet device according to claim 1, wherein:

the tail cap core and the body are provided with snap fit structures for defining the position of the tail cap where the elastic force of the driving spring is the minimum.

7. The lancet device according to claim 1, wherein:

one of the tail cap and the body is provided with a thread, the other of the tail cap and the body is provided with a thread cooperation portion, the thread is in interference fit with the thread cooperation portion, or the thread and the thread cooperation portion are additionally provided with snap fit structures, and the snap fit structures are configured to limit a relative axial position between the tail cap and the body.

8. The lancet device according to claim 1, further comprising:

a head cap, wherein a first end of the head cap is provided with the needle outlet hole, and a second end of the head cap is connected to the first end of the body.

9. The lancet device according to claim 8, wherein:

a first end of the needle seat is provided with elastic arms that are evenly distributed in the circumferential direction, and the elastic arms elastically abut against an inner wall of the head cap or are provided to an annular wall in the head cap.

10. The lancet device according to claim 9, wherein:

the lancet device further comprises a return spring, and the return spring is adapted to abut against between the head cap and the needle seat to provide an elastic force for retracting the ejected blood taking needle into the head cap.

11. The lancet device according to claim 10, wherein:

the elastic arms are provided to the annular wall in the head cap in an elastic abutting manner, and a space applicable to accommodating the return spring is defined between the annular wall and the inner wall of the head cap.

12. The lancet device according to claim 1, further comprising:

a stop block provided at a second end of the needle seat, and the stop block comprising a column and a stop surface, wherein the stop block cooperates with a corresponding blocking surface in the lancet device to define a movement position of the needle seat toward the needle outlet hole, wherein the stop block comprises an elastomer.

13. A lancet device comprising:

a body, having a first end and a second rear end;

a head cap, wherein a first end of the head cap is provided with a needle outlet hole, and a second end of the head cap is connected to the first end of the body;

a tail cap provided at a distalmost end of the device opposite the blood taking needle, the tail cap comprising a tail cap housing and a tail cap core, wherein the tail cap core being provided with a threaded connection portion that is in threaded connection with the second end of the body, and the tail cap is provided with a first spring connecting portion;

a needle core assembly, at least a part of which is axially guided and located in the body, wherein the needle core assembly includes a needle seat having a first end and a second end, the blood taking needle is adapted to be provided to the needle seat, and a needle tip of the blood taking needle is adapted to extend out from the needle outlet hole;

a driving core acting on the needle seat, wherein the driving core is adapted to drive the needle seat to move toward the needle outlet hole based on a trigger operation, and the driving core is provided with a second spring connecting portion;

a driving spring for providing a trigger elastic force for the needle seat to move toward the needle outlet hole, wherein a first end of the driving spring is configured to abut against or connect with the second spring connecting portion of the driving core, a second end of the driving spring is configured to abut against or connect with the first spring connecting portion of the tail cap, and the driving spring is located between the first spring connecting portion of the tail cap and the second spring connecting portion of the driving core;

the tail cap core being divided into two parts, a proximate end and a distal end, by a separation piece, wherein compression of the driving spring is limited by the separation piece, the separation piece comprising a proximate and distal end face, and the proximate end face of the separation piece is configured to abut against the second rear end face of the body, and the elastic force is the maximum at this position; and a stop block provided at the second end of the needle seat, and the stop block comprising a column and a stop surface, wherein the stop block cooperates with a corresponding blocking surface in the lancet device to define a movement position of the needle seat toward the needle outlet hole, wherein the stop block comprises an elastomer, wherein the tail cap core is provided in the tail cap housing in a manner of being able to axially move relative to the tail cap housing without relative rotation; and wherein the tail cap is configured to be rotatable relative to the body to adjust an axial distance between the first spring connecting portion and the second spring connecting portion, to adjust the trigger elastic force of the driving spring.

* * * * *